United States Patent [19]

Kikugawa et al.

[11] 4,130,642
[45] Dec. 19, 1978

[54] METHOD OF SEPARATING BLOOD CELLS COMPONENTS

[75] Inventors: Kiyomi Kikugawa, Mino; Kyoko Minoshima, Tokyo, both of Japan

[73] Assignee: Terumo Corporation, Tokyo, Japan

[21] Appl. No.: 846,369

[22] Filed: Oct. 28, 1977

[30] Foreign Application Priority Data

Nov. 2, 1976 [JP] Japan ................................ 51-132191

[51] Int. Cl.$^2$ ...................... A61K 35/14; A61K 35/18
[52] U.S. Cl. .................................................... 424/101
[58] Field of Search ......................................... 424/101

[56] References Cited

PUBLICATIONS

Flewing — Brit. J. of Experimental Pathology, vol. 7, (1926), pp. 281–286.
Diepenhorst et al. — Vox Sanguinus, vol. 23, (1972), pp. 308–320.

*Primary Examiner*—Sam Rosen
*Attorney, Agent, or Firm*—Bacon & Thomas

[57] ABSTRACT

A method of separating blood cell components, characterized in that a blood cells suspension containing red cells and at least one of leucocytes and blood platelets is passed through a processing column packed with an Egyptian cotton which has been de-fatted and bleached, thereby allowing the blood cells components other than the red cells to be adsorbed substantially completely on the Egyptian cotton and permitting the red cells portion alone to be isolated.

10 Claims, 2 Drawing Figures

U.S. Patent        Dec. 19, 1978        4,130,642
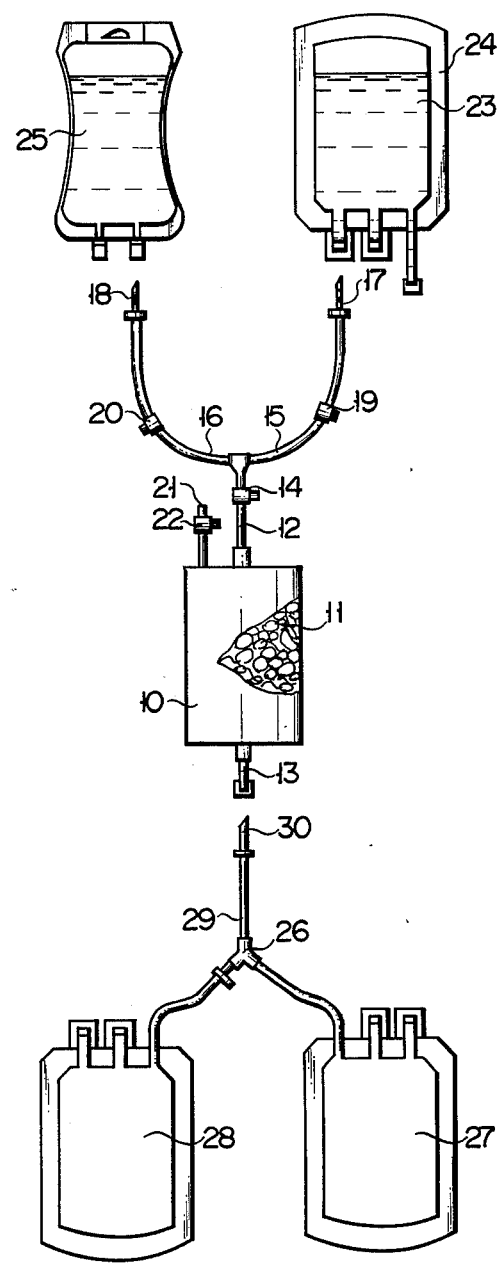

METHOD OF SEPARATING BLOOD CELLS COMPONENTS

BACKGROUND OF THE INVENTION

This invention relates to a method of separating blood cells components, particularly, to a method of isolating the red cells portion for use in blood component transfusion and biochemical examination.

It was customary in the past to use the whole blood in the blood transfusion therapy. Recently, a so-called "blood component transfusion", namely, the therapy utilizing the transfusion of the required blood component alone, has come to be put into practice in accordance with the progress of medical treatments. However, the blood component transfusion is not extensively employed nowadays because it is difficult to prepare the required blood component in a sufficient amount. In the case of, for example, red cells transfusion, it is difficult to isolate red blood cells substantially free from leukocytes having HL-A type antigens and blood platelets having platelet antigens.

Presently, the following methods of isolating red blood cells are known to the art:
(1) Inverted centrifugation
(2) Washing with physiological saline solution
(3) Sedimentation of red cells using dextrane or hydroxyethyl starch (HES)
(4) Passage through a nylon column
(5) Reconstitution of frozen and thawed blood Incidentally, the above-noted methods are described in "Blood Component Therapy" edited by American Association of Blood Banks, Twentieth Century Press, Inc., Chicago, U.S.A., page 9, 1969.

Method (3) noted above is actually employed for preparing leukocyte-poor red cells, but leaves room for improvement with respect to the recovery rate of red cells and removals of leukocytes and blood platelets. In addition, a problem remains unsolved concerning the antigenic property of the sedimentation agent. The other methods are not satisfactory in terms of removal rates of leukocytes and blood platelets.

Further, it is reported in "British Journal of Experimental Pathology, Vol. 7, pp. 281-286, 1926" that Flewing has found adsorption capability of leukocytes on cotton fibers. Based on this finding, Diepenhorst et al have attempted to prepare leukocytes-poor red cells by using medical strings (1 g/m) of cotton fibers as the leukocyte adsorbent, as reported in "Vox Sanguinus, Vol. 23, pp. 308-320, 1972". However, the adsorption method proposed by Diepenhorst et al is not satisfactory in the following:

(1) It is necessary to use a large amount of the adsorbent cotton strings. Specifically, 50g of the adsorbent strings packed at a density of 50 g/300 ml are used for processing 500 ml of the whole blood or red cells suspension.

(2) It is necessary to apply 0.5 to 0.7 kg/cm$^2$ of pressure for passing the blood through the processing column and about one hour is required for processing 500 ml of blood.

(3) The requirement of high pressure application renders it difficult to use a blood bag made of polyvinylchloride.

(4) The blood platelet removal rate is as low as 20 to 30%, though it is possible to remove 95% of leukocytes. The value of 95% seems reasonably high, but it is necessary to use a large amount of cotton strings for processing a unit volume of blood as mentioned in item (1) above. In other words, the leukocyte adsorption efficiency is not satisfactorily high.

Still further, U.S. Pat. No. 3,462,361 discloses a method of separating leukocytes from the whole blood by adsorption of leukocytes on synthetic fibers such as nylon and polyesters. However, the method disclosed in this U.S. Pat. is incapable of removing sufficiently the blood platelet and lymphocytes accounting for about 20-30% of the leukocytes by way of adsorption and, thus, unsuitable for isolating the red cells portion alone.

SUMMARY OF THE INVENTION

This invention has been achieved to overcome the difficulties inherent in the prior arts in this field. Specifically, an object of this invention is to provide a method of separating substantially perfectly blood cells suspension containing red cells and at least one of leukocytes and blood platelets into the red cells portion and the leukocyte and/or blood platelet portion.

Another object is to provide a method of selectively taking out the red cells portion substantially free from impurities including coloring materials by using an apparatus simple in structure and easy to operate.

According to this invention, there is provided a method of separating blood cells components, characterized in that a blood cells suspension containing red cells and at least one of leukocytes and blood platelets is passed through a processing column packed with an Egyptian cotton which has been de-fatted and bleached, thereby allowing the blood cells components other than the red cells to be adsorbed substantially completely on the Egyptian cotton and permitting the red cells portion alone to be isolated.

BRIEF DESCRIPTION OF THE DRAWING

The appended drawing shows an apparatus used for separating blood cells components according to one embodiment of this invention.

DETAILED DESCRIPTION OF THE PREFERRED EMBODIMENT

Cotton fibers can be roughly classified into three kinds, i.e. Egyptian cotton (or, scientifically termed "*Gossypium barbadense*"), American or Up-land cotton (or, scientifically termed "*Gossypium hirsutum*"), and Asian or Indian cotton (or, scientifically termed "*Gossypium atrboreum* or *Gossypium herbaceum*"). Table 1 below shows the average fiber length, average fiber thickness and average number of twistings per unit length of fiber for these cotton fibers.

Table 1

| | Average length (mm) | Average thickness ($\mu$) | Average number of twistings per cm |
|---|---|---|---|
| Egyptian cotton | 35.6 | 16.3 | 70-112 |
| American cotton | 25.4 | 20 | 56-96 |
| Asian cotton | 20 | 21 | 48-76 |

Table 1 shows that Egyptian cotton is largest and Asian cotton is smallest in the average length of fiber. In contrast, Egyptian cotton is smallest and Asian cotton is largest in the average thickness of fiber. The surgical cotton or "purified cotton" (U.S. Pharmacopeia) available on the U.S. market is made of American cotton.

Through extensive research, the present inventors have found that Egyptian cotton composed of fine and long cotton fibers is prominently superior to Asian cotton and American cotton both composed of thick and short cotton fibers in either the leukocyte removal or the blood platelet removal. In general, Egyptian cotton is not used for the medical purpose. In this sense, it is quite interesting that the present inventors have found a new use of Egyptian cotton for the medical purpose.

It is preferred that the Egyptian cotton used in this invention be at least 26.0mm in fiber length and 13 to 19μ in fiber thickness, particularly, at least 35mm in fiber length and 13 to 16μ in fiber thickness. It is also preferred that the Egyptian cotton be subjected to de-fatting and bleaching prior to the use because the natural Egyptian cotton tends to liberate impurities including coloring materials into the blood under processing and is low in affinity for water. Incidentally, the treated Egyptian cotton is just the same as the natural Egyptian cotton in the separation effect of blood cells components.

The de-fatting and bleaching mentioned above is carried out by treating the natural Egyptian cotton with caustic soda, followed by treatment with a hypochlorite, or by caustic soda treatment, followed by treatment with hydrogen peroxide, as in a general method of preparing a surgical cotton. By this treatment, the impurities contained in the natural Egyptian cotton are removed, resulting in that the coloring materials and other impurities originally contained in the cotton do not flow into the blood under processing.

Any type of blood cells suspension can be treated by the method of this invention, provided that the suspension contains red cells and at least one of leukocytes and blood platelets. For example, the invented method can be applied to the processing of the fresh whole blood mixed with a suitable anticoagulant, or to the processing of packed red cells.

Suitable anticoagulants added to the fresh whole blood include, for example, heparin, ACD (Acid-Citrate-Dextrose) solution, and CPD (Citrate-Phosphate-Dextrose) solution. When the invented method is applied to the processing of packed red cells, physiological saline solution may be added to a packed red cells, so as to adjust the haematocrit value of the packed red cells to range from 40 to 60. It is also preferred that the temperature of the blood cells suspension under processing be controlled to fall within the range of from 4° C. to 37° C., particularly, between 4° C. and 10° C.

It suffices in this invention to use the de-fatted and bleached Egyptian cotton at the rate of 5 to 20g per 200ml of the whole blood or the blood cells suspension which is to be processed. It is recommended that the de-fatted and bleached Egyptian cotton be packed in a processing column at a bulk specific gravity of 0.1 to 0.4 and, in general, to form a bed of 10 to 80ml. For the case of processing 200ml of the whole blood or the red cells suspension, the gauge pressure required for passing the blood through the column is at most 0.2 kg/cm$^2$ and the required processing time is as short as 10 to 30 minutes. The low gauge pressure mentioned renders it possible to form a closed system by connecting a general type of blood bag formed of polyvinylchloride to the processing column packed with the de-fatted and bleached Egyptian cotton, resulting in an easy operation for separating the blood cells components.

As seen from the Examples described later, the method of this invention permits at least 98% of the red cells recovery and at least 98% of leukocyte removal and blood platelet removal from the whole blood or the blood cells suspension. Further, when distilled water or physiological saline solution is passed through the bed of the de-fatted and bleached Egyptian cotton used in this invention as an adsorbent, dissolusion of fine particles from the Egyptian cotton into the liquid is scarcely recognized. To be more specific, particles greater than 2μ are hardly detected when the liquid which has passed through the bed is observed by a microscope. Still further, when the effluent from the bed is tested in accordance with the standard set forth for the examination of cellulose type dialysis membrane used for a dialysis type artificial kidney, each of ultraviolet absorption material, pH-changing material and heavy metals is found satisfactory. It is also important to note that, when the blood is passed through the treating column packed with the de-fatted and bleached Egyptian cotton, the effluent from the column is found satisfactory with respect to the hemolysis test and acute virulence test for the test methods of plastic vessels for transfusion liquid specified in the Japanese Pharmacopoeia, 9th Revision. Clearly, the blood cells component separated by the method of this invention is free from any particular medical problem.

The appended drawing shows an apparatus for embodying the method of this invention and described in the following is how to separate the blood cells components from the whole blood or the blood cells suspension such as packed red cells, with reference to the appended drawing.

As shown in the drawing, a cylindrical column 10 formed of a hard thermoplastic material or the like is packed with a de-fatted and bleached Egyptian cotton 11. Tubes 12 and 13 are connected to the upper and lower faces of the column 10, respectively. Further, a flow control clamp 14 is mounted at the upper portion of the upper tube, or inlet tube 12, and another tube branched into tubes 15 and 16 is connected to the flow control clamp 14. It is seen that cannulas 17 and 18 are mounted to the tips of the tubes 15 and 16, respectively, and clamps 19 and 20 are also provided for controlling the flow of the fluid through the tubes 15 and 16, respectively.

Reference numeral 21 shown in the drawing denotes an air inlet port, which is provided with an air filter and used for controlling the interior pressure of the column 10. Needless to say, the open air is introduced or released from the air inlet port 21, as required, during the operation of the apparatus. Incidentally, the air flow through the inlet port 21 is controlled by a flow control clamp 22. Indeed, the air inlet port 21 is convenient, but is not necessarily required in this invention.

In performing the blood component separating operation by using the above-described apparatus, the cannula 17 is connected to a polyvinyl chloride bag 24 housing 200ml of blood 23 to be processed. Likewise, the cannula 18 is connected to a polyvinylchrolide bag 25 housing physiological saline solution. Further, two vacant polyvinylchloride bags 27, 28 are disposed downstream of the processing column 10. As shown in the drawing, a tube 29 is connected to these bags 27, 28 via a branched tube 26 and a cannula 30 mounted to the tip of the tube 29 is connected to the outlet tube 13 of the column 10. When the four bags 24, 25, 27 and 28 have been connected to the processing column 10 in the above-noted fashion, 50 to 100ml of the physiological saline solution housed in the bag 25 is passed first through the processing column so as to equilibrate the de-fatted and bleached Egyptian cotton 11 packed in the processing column. Namely, the clamps 20 and 14 are opened with the clamp 19 kept closed, thereby introducing the physiological saline solution housed in the bag 25 into the column 10. The solution passing through the column 10 flows into the vacant bag 27 through the outlet tube 13 of the column 10.

Then, the clamp 20 is closed and the clamp 19 opened so as to allow the blood 23 housed in the bag 24 to flow through the processing column, the processed blood which has passed through the column being collected in the other vacant bag 28 through the outlet tube 13 of the treating column. Where packed red cells are processed, the haematocrit value of the packed red cells may be adjusted 40 to 60 prior to introduction of the packed red cells into the column 10. To this end, the clamps 19 and 20 are opened with the clamp kept closed so as to introduce the physiological saline solution housed in the bag 25 into the blood bag 24.

After all the blood 23 housed in the bag 24 has been passed through the column 10, the clamp 19 is closed again and the clamp 20 opened, thereby washing the Egyptian cotton 11 packed in the column 10 with the physiological saline solution and collecting the residual red cells in the bag 28.

In the embodiment described, the bags housing the blood and the physiological saline solution are both made of a soft thermoplastic material such as polyvinylchloride. In this case, the flow of the fluid through the Egyptian cotton acting as the absorbent can be promoted by applying a gauge pressure of as low as about 0.2 kg/cm$^2$ to either of these bags.

The apparatus shown in the appended drawing permits preparing the leukocyte-poor red cells in about 10 to 30 minutes from 200ml of the whole blood or packed red cells. At least 98% of leukocytes and blood platelets can be removed and at least 98% of red cells can be recovered through the prescribed operation. In addition, the recovered red cells are substantially equal to those before the processing in morphology recognized by electron microscopic observation, the contents of adenosine-5'-triphosphate and 2,3-diphosphoglyceric acid, and osmotic fragility curve.

Further, hemolysis is not recognized at all in the recovered red cells. It should also be noted that, where an ACD solution, a CPD solution or the like has been added to the blood before the processing, the recovered red cells are substantially equal in the above-noted properties to those contained in the whole blood after 21 days of storage at 4° C., i.e. the storage of both the recovered red cells and the whole blood.

As described in detail, the method of this invention uses an Egyptian cotton as the adsorbent and permits removing substantially completely the leukocyte and blood platelet both containing tissue antigens, thereby isolating the red cells satisfactorily. In addition, since the operation is based principally on a simple filtration, the apparatus used for the separating operation is very simple in structure and can be operated quite easily, providing a prominent economic advantage.

Described in the following are Examples of this invention in comparison with the prior art.

CONTROL 1

Blood processing columns were packed with each of an Egyptian cotton (or, scientifically termed "*Gossypium barbadense*"), an American cotton (or, scientifically termed "*Gossypium hirsutum*") and a surgical cotton made of an Indian cotton (or, scientifically termed "*Gossypium herbaceum*") at a packing density of 12g/40ml. Incidentally, the properties of the cottons used as shown in Table 1 presented previously.

On the other hand, 200ml of packed red cells were treated with physiological saline solution so as to adjust the haematocrit value at 50 and, then, passed through each of the treating columns. The resultant values of the red cells recovery rate, leukocyte removal rate and the blood platelet removal rate are shown in Table 2 below.

Table 2

| Adsorbent | Red cells recovery rate (%) | Leukocyte removal rate (%) | Platelet removal rate (%) |
|---|---|---|---|
| Egyptian cotton | 98 | 98 | 98 |
| Egyptian cotton (de-fatted and bleached) | 98 | 99 | 98 |
| American cotton | 98 | 80 | 89 |
| American cotton (de-fatted and bleached) | 99 | 83 | 90 |
| Asian cotton | 98 | 62 | 30 |

The packed red cells before the processing contained 4,000,000 to 5,000,000 red cells per mm$^3$, 2,000 to 5,000 leukocytes per mm$^3$ and 70,000 to 200,000 blood platelets per mm$^3$.

EXAMPLE 1

De-fatted and bleached Egyptian cotton having a fiber length of at least 35mm, a fiber thickness of 13 to 16$\mu$ and 100 twistings per cm was packed as the adsorbent in the processing column of an apparatus as shown in the appended drawing. Then, 200ml of packed red cells treated with physiological saline solution to have a haematocrit value of 50 was passed through the treating column under atmospheric pressure. Tables 3 and 4 below show the resultant values of the red cells recovery rate, leukocyte removal rate, blood platelet removal rate and the properties of the recovered red cells. Incidentally, Table 4 shows changes with time for case 1 of Table 3.

Table 3

| Case | Packing density of adsorbent | Required treating time | Red cells recovery rate | Leukocyte removal rate | Platelet removal rate |
|---|---|---|---|---|---|
| 1 | 12g/40ml | 20 minutes | 98% | 98% | 98% |
| 2 | 10g/35ml | 20 " | 100" | 98" | 98" |
| 3 | 12g/50ml | 20 " | 98" | 99" | |

Table 4

| | Storage time | ATP $\mu$ mol/g hemoglobin | DPG $\mu$ mol/g hemoglobin | Hemolysis |
|---|---|---|---|---|
| Unprocessed | 0 | 3.9 | 8.6 | None |
| Recovered red cells | 0 | 4.0 | 8.3 | None |
| Unprocessed | 7 days* | 3.8 | 4.2 | None |
| Recovered red cells | 7 days* | 4.0 | 3.8 | None |

*Stored at 4° C

EXAMPLE 2

De-fatted and bleached Egyptian cotton having a fiber length of at least 35mm, a fiber thickness of 13 to 16$\mu$ and 100 twistings per cm was packed in the processing column of an apparatus as shown in the appended drawing at a packing density of 12g/40ml. Then, 200ml of heparin-added fresh whole blood was passed through the processing column, obtaining the result that the red cells recovery rate was 99%, the leukocyte removal rate was 99% and the blood platelet removal rate was 98%.

What is claimed is:

1. A method of separating blood cells components, comprising the step of passing blood cells suspension containing red cells and at least one of leukocytes or blood platelets through a column packed with a de-fatted and bleached Egyptian cotton so as to allow the blood cells components other than red cells to be adsorbed on the Egyptian cotton and to isolate the red cells portion alone.

2. The method according to claim 1, wherein the Egyptian cotton has a fiber length of at least 26mm, an average fiber thickness of 13 to 19$\mu$ and the number of twistings per cm of 70 to 112.

3. The method according to claim 2, wherein the Egyptian cotton has an average fiber length of at least 35mm and an average fiber thickness of 13 to 16$\mu$.

4. The method according to claim 1, wherein the Egyptian cotton is packed in the column at a bulk specific gravity of 0.1 to 0.4.

5. The method according to claim 1, wherein the Egyptian cotton is packed in the column at the rate of 5 to 20g per 200ml of the blood cells suspension to be processed.

6. The method according to claim 1, wherein the blood cells suspension brought into contact with the Egyptian cotton is maintained at 4° to 37° C.

7. The method according to claim 6, wherein the blood cells suspension is maintained at 4° to 10° C.

8. The method according to claim 1, wherein the blood cells suspension is selected from the group consisting of the whole blood subjected to an anticoagulation treatment and packed red cells.

9. The method according to claim 8, wherein physiological saline solution is added to the packed red cells to adjust the haematocrit value at 40 to 60 and, then, the packed red cells are passed through the column.

10. The method according to claim 1, wherein a gauge pressure of about 0.2kg/cm$^2$ is applied to the blood cells suspension for passing the suspension through the column.

* * * * *